United States Patent [19]

Blomqvist et al.

[11] Patent Number: 5,571,138
[45] Date of Patent: Nov. 5, 1996

[54] SURGICAL STRETCHING DEVICE FOR THE EXPANSION OF TISSUE

[75] Inventors: Gunnar Blomqvist, Västra Frölunda; Hans Hellström, Onsala, both of Sweden

[73] Assignee: Stretchex AB, Sweden

[21] Appl. No.: 364,845

[22] Filed: Dec. 23, 1994

Related U.S. Application Data

[63] Continuation of Ser. No. 108,691, filed as PCT/SE92/00121, Feb. 28, 1992, abandoned.

[30] Foreign Application Priority Data

Mar. 6, 1991 [SE] Sweden ................................. 9100666

[51] Int. Cl.⁶ .............................. A61B 17/08; A61D 1/00
[52] U.S. Cl. ............................................ 606/218; 606/213
[58] Field of Search ... 606/1,217,213,215–221,232,233

[56] References Cited

U.S. PATENT DOCUMENTS

| | | | |
|---|---|---|---|
| 3,926,193 | 12/1975 | Hasson | 606/218 |
| 3,971,384 | 7/1976 | Hasson | 606/218 |
| 5,127,412 | 7/1992 | Cosmetto et al. | 606/218 |

FOREIGN PATENT DOCUMENTS

| | | |
|---|---|---|
| 0279534A1 | 8/1988 | European Pat. Off. |
| 0324234B1 | 7/1989 | European Pat. Off. |
| 1147363 | 3/1985 | U.S.S.R. ................. 606/132 |
| 1153895 | 5/1985 | U.S.S.R. ................. 606/218 |

*Primary Examiner*—Gary Jackson
*Assistant Examiner*—Glenn Dawson
*Attorney, Agent, or Firm*—Lerner, David, Littenberg, Krumholz & Mentlik

[57] ABSTRACT

The present invention relates to a surgical stretching device for the expansion of tissue, in particular for the expansion of skin. The invention is characterized in that it includes one or more threads (1) or bands (1) extending between two fastening arrangements (2). The fastening arrangements have one-way nips for the threads (1) or the bands (1) so that at least one fastening arrangement (2) can be moved on the threads (1), or bands towards the other fastening arrangement. When this happens, the distance between fastening points on the tissue is reduced such that a stretching of the tissue occurs outside the fastening points.

8 Claims, 1 Drawing Sheet

SURGICAL STRETCHING DEVICE FOR THE EXPANSION OF TISSUE

This is a continuation of application Ser. No. 08/108,691, filed Sep. 3, 1993, now abandoned.

TECHNICAL FIELD

The present invention relates to a surgical stretching device for the expansion of tissue, in particular for the expansion of skin in connection with surgical operations.

1. The Problem

Due to skin damage or where scars or birthmarks are on the skin or where the skin has other defects in any other place, it is often necessary to remove the defective parts and to replace them. A large problem with such surgical operations is to procure sufficient healthy skin to be transplanted onto the place where the defective skin has been removed. One can take skin from for example the thigh on humans and transplant this. If however skin is taken from such a healthy part of the body then the whole skin can often not be taken but only the outer part of this and the transplant is therefore not a perfect replacement. The transplanted skin is thinner and lacks the lower layer. The reason that the skin cannot be taken completely from a healthy part is that the skin in this part must have the possibility to grow back again.

2. Technical Background

However there are methods for achieving perfect replacement material, e.g. skin, when necessary. The body is allowed to produce this skin itself in that a tissue expansion of the skin is achieved at a convenient location. This expansion is brought about normally under narcosis by implanting an expanding prosthesis, i.e. a silicon balloon with a filling nipple, under the skin and filling this afterwards with salt solution in order to achieve expansion and growth of the skin. To obtain a sufficient amount of skin, new fluid has to be added to the bladder at equal intervals via an implanted filling valve. This happens during visits to the surgeon each week for several months. This method of tissue expansion is called the Radovan-tissue-expansion method and started being applied in the 1970's. When sufficient skin has formed, the defective skin or the alteration is removed and the expanded skin is introduced into the defect and is sewn into place after removal of the expanded prosthesis. This is an inconvenient method to produce replacement tissue which means that the patient is put to sleep twice and inbetween visits the doctor once a week for several months. This method and means for performing it is described in EP 0 324 234. Another method is described in EP 0 279 534. In this method an apparatus is used comprising two pins inserted into the skin and connected to each other by a tensioning, flexible strap.

3. The Solution

For a long time it has therefore been desired to achieve a device for expansion of tissue in an easier way which is cheaper and quicker as well as being less difficult for the patient than the known manner. According to the present invention a surgical stretching device for tissue expansion has therefore been achieved, in particular for the expansion of skin, said stretching device including one or more threads, or bands with a fastening arrangement for the threads, or bands for e.g. the skin, at at least one end of the threads, or bands and another fastening arrangement for fastening at another fixing point on e.g. the skin or at some other arrangement at the other end whereby at least one of the fastening arrangements comprises one-way nips or similar for the threads or the bands so that at least the one fastening arrangement can be moved on the threads, or bands towards the other fastening arrangement and thereby reduce the distance between the fastening points such that a stretching of the tissue occurs outside the fastening points, the device being characterized in that the fastening arrangements each consist of an elongate body with an arched cross-section and through-holes for the bands or threads as well as blocking devices surrounding the threads or bands in gripping contact on the concave side of the arch.

In accordance with the invention it is preferable that the stretching device comprises a plurality of bands, threads or the like which are introduced into a fastening arrangement which is common for all bands or threads.

It is preferred that the blocking devices are made in one piece with the elongate body, but they can also be composed of separate units.

According to the invention the blocking devices can also consist of rotatable and lockable knobs or the like for winding up the threads.

According to the invention it is preferred that the bands or threads have a stiff curved part in the central area.

According to the invention it is preferred to make the fastening arrangements and bands in plastic and that the threads or bands are curved, but not appreciably extensible. The bands can also be stiff and made from rods.

DESCRIPTION OF THE FIGURES

The invention will be described in more detail with reference to the accompanying drawings in which.

DETAILED DESCRIPTION OF THE INVENTION

Figure 1:
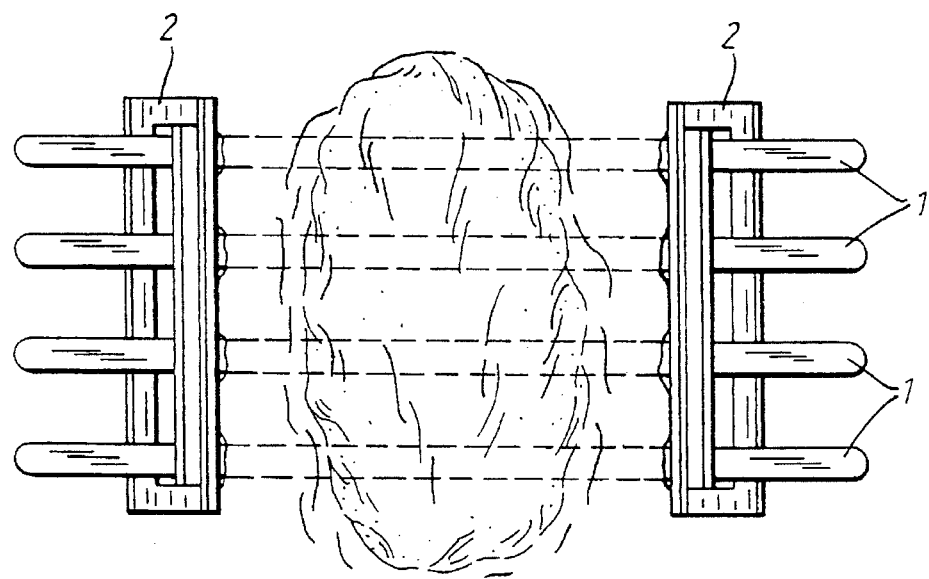
FIG. 1 shows a stretching device according to the invention seen from above.

In FIG. 1 which shows a preferred embodiment of the invention there are shown four bands 1 which have both ends inserted into fastening arrangements 2 which are similar. The number of bands can vary depending on how large an area of skin is to be removed from between the fastening arrangements. The bands between the fastening arrangements are stretched since they are located beneath the skin in use. The surgeon, who shall use the stretching devices according to the invention, implants the bands or threads 1 under the skin by making channels under the skin. At the ends of the channels where the bands stick up the fastening arrangements 2 are attached, that clamp round the ends. The fastening arrangements are drawn towards each other as far as possible before they are fixedly clamped. In this way the skin outside the fastening arrangements is stretched and the skin between the fastening arrangements is pressed together. After a while the fastening arrangements 2 can be moved towards each other again and thus stretch the skin outside these additionally. This is possible due to the fact that the stretched skin expands quickly under tension. After a time, which can be a week or somewhat longer depending on how large an area of skin has to be removed, i.e. the area between the fastening arrangements, the skin outside the fastening arrangements has been stretched so much that the fastening arrangements almost meet together. They can then be removed, the bands or threads can be withdrawn, the unhealthy portion between the fastening devices 2, which has now become very small and crumpled together, can be removed after which the stretched healthy skin parts outside the fastening arrangements can be sewn together.

Figure 2:
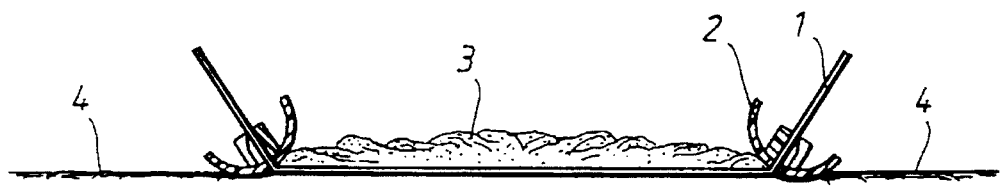
FIG. 2 shows the same device partly in section seen from the side and FIG. 3 shows an enlargement of the fastening devices partly in section

FIG. 2 shows the arrangement according to the invention seen from the side. The bands 2 are implanted into the skin 3 which is crumpled together between the fastening arrangements 2. The healthy skin parts 4 outside the fastening arrangements 2 are thus stretched.

Figure 3:
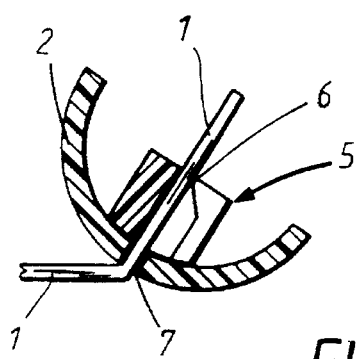

FIG. 3 shows an enlarged sectional view through a fastening arrangement 2. As is clear from FIG. 1 this is elongated and presents an arched shape in cross section. Inside the arch there is a blocking device 5 which clamps around the band 1 at the point 6. On pulling the band 1 at the same time as holding the blocking arrangement 5 pressed against the concave side of the fastening arrangement 2, the band 1 will be displaced outwardly with respect to this at the same time as this is locked against being moved in the other direction. The tensioning of the band 1 can thereby be achieved. Holes 7 are made in the fastening arrangements 2 for through-movement of the bands or threads.

Figure 4:
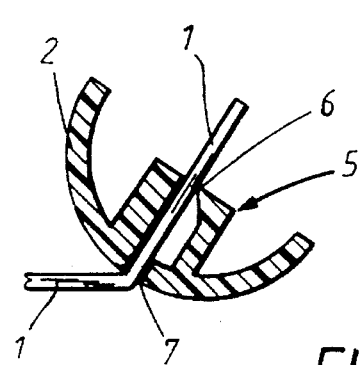
FIG. 4 shows an enlargement of an alternative embodiment of the fastening devices partly in section.

The invention has been described above with reference to a preferred embodiment. This can be varied in such a manner that the blocking devices 5 for example can be separate pieces or as shown in FIG. 4, such that they are made in one piece with the fastening arrangements 2. A suitable material from which these can be manufactured is plastic and likewise for the bands.

The requirement this material has to meet is that the skin or the human body can accept these materials and that they can be sterilised. It is also preferred that the bands or threads are bendable but they should not be appreciably extensible which would mean that the stretching forces are weakened. Even stiff, rod-like material can be used.

The blocking devices can also be made as rotatable knobs around which the threads 1 are wound. This embodiment is thus not suitable for bands. In order that the rotatable knobs can maintain the stretching forces they must be lockable.

The blocking devices can also comprise screws for fixedly locking the threads or bands. One advantage with such a blocking device is that it can be slackened if necessary. A combination of screws and catches in the same blocking devices can also be useful, or one could arrange a blocking device with a screw at the one end and a blocking device with a catch at the other.

Instead of having a blocking device movable along the threads or bands at both ends, the bands or threads can be foreseen with a simple stop at one end. The stretching of the bands or threads then occurs only at the other end.

In a further embodiment of the invention the fastening arrangements are foreseen with hook-like projections on the underside. These hooks can be introduced into the skin and this gives thus the possibility of allowing the threads or bands to lie completely externally on the skin. The advantage is thereby attained that channels under the skin do not need to be made. The skin between the fastening arrangements will of course be removed later. One disadvantage of this embodiment is however that the skin between the fastening arrangements folds up and will press against the bands 1. It is therefore suitable if the these bands are stiff in the middle portion and are curved outwardly so that space for the folded up skin is created.

According to a further embodiment, the fastening arrangements can be attached to the skin with the help of suitable adhesive which gives a secure anchoring and which can be maintained for sufficiently long time. In such a case one can wait completely with surgical operation until the piece of skin between the fastening arrangements is to be removed. With this embodiment the adhesive can be attached to the underside of the fastening arrangements in advance and be protected by means of a suitable tape which can be removed.

The stretching device according to the invention can also be used in such a way that instead of anchoring to the skin at both ends, the one end can be anchored to, for example, a "spike" implanted in the skeletal structure which sticks out through the skin and the other end to the skin. The skin is of course then stretched in one direction only. This can be advantageous for example on stretching of the skin of the thigh where a spike in the hip can be used to fasten the stretching device at one end and a normal fastening arrangement to the skin at the other end, whereby the stretching of the skin will occur upwardly in the same way as when one pulls up a stocking.

The invention has been described above in relation to expansion of skin tissue. It is of course possible to apply it also for expansion of other types of tissue such as muscle or the like. The stretching device then has to be implanted which is fully possible.

The stretching device according to the invention can be used for stretching of skin on almost the whole body. It is of course particularly suitable for stretching of the skin on the arms and legs. This is particularly advantageous since the prior art expanding methods using the Radovan expansion prosthesis often give unsuccessful results on these parts of the body.

The stretching arrangement according to the present invention is cheap to manufacture and the use of it results in very low costs compared to prior art methods. It also means an entire very mild treatment for the patient.

In summary one can say that the invention gives the following advantages compared with prior art methods:

1. The stretching device can be applied under local anaesthetic.
2. The patient him/herself is normally able to take care of the expansion.
3. Quick expansion
4. Expansion from two directions.
5. Very cost-economic.

We claim:

1. A surgical stretching device for the expansion of tissue comprising at least one band means having a first end and a second end, said band means being implantable through a channel under the skin with said first and second ends of said band means sticking up through said skin at opposite ends of said channel;

first and second anchoring means, each comprising an elongated body, said first anchoring means including a first aperture means for receiving said first end of said band means, said second anchoring means including a second aperture means for receiving said second end of said band means and each of said anchoring means including a first surface and a second surface with said first surfaces of said first and second anchoring means facing each other with said band means therebetween, each of said anchoring means further including a means for removably attaching each anchoring means to said tissue; and a first one-way tightening means for fixedly clamping said first anchoring means to said first end of said band means passing through said first aperture means, and a second one-way tightening means for fixedly clamping said second anchoring means to said second end of said band means passing through said second aperture means, wherein said first and second one-way tightening means clamps said first and second anchoring means to said first and second ends of said band means outward of said second surfaces of said first and second anchoring means;

so that by implanting said band means through said skin channel, attaching said anchoring means to said skin, passing said first and second ends of said band means through said first and second aperture means, drawing together said first surfaces of said first and second anchoring means as close together as possible and clamping said first and second anchoring means to said first and second ends of said band means with said first and second one-way tightening means, said first and second anchoring means are secured to said skin at said opposite ends of said channel and stretch the skin outside said second surfaces of said first and second anchoring means so that said skin between said first surfaces of said first and second anchoring means under which said band means is implanted is pressed together;

whereby said first and second one way tightening means allow only one-way movement of said first and second ends of said band means through said first and second aperture means of said first and second anchoring means outwardly from said second surfaces of said first and second anchoring means, so that outward displacement of said first and second ends of said band means moves said first surfaces of said first and second anchoring means towards each other, thereby additionally stretching said skin outside said second surfaces of said first and second anchoring means.

2. The surgical stretching device of claim 1, comprising:

a plurality of band means each having a first end and a second end;

a plurality of first and second aperture means on said first and second anchoring means, respectively, for said first and second ends of each band means to pass through said respective first and second anchoring means; and a plurality of first and second one-way tightening means for fixably clamping said respective first and second anchoring means to each first and second end of each band means passing through said respective first and second aperture means.

3. The surgical stretching device of claim 2, wherein each said band means are plastic.

4. The surgical stretching device of claim 2, wherein each first and second end of said plurality of band means comprises a plurality of threads.

5. The surgical stretching device of claim 1, wherein said first and second one-way tightening means are unitary with said first and second anchoring means, respectively.

6. The surgical stretching device of claim 1, wherein said first and second one-way tightening means are separate units with respect to said first and second anchoring means, respectively.

7. The surgical stretching device of claim 1, wherein said band means are substantially inextensible.

8. The surgical stretching device of claim 1, wherein said first and second surfaces of each of said first and second anchoring means have a convex surface and a concave surface, respectively, so that said elongated body of each of said first and second anchoring means has an arcuate cross-sectional shape, and said first and second one-way tightening means comprise first and second blocking means disposed on said concave surface of said first and second anchoring means, respectively.

* * * * *

UNITED STATES PATENT AND TRADEMARK OFFICE
CERTIFICATE OF CORRECTION

PATENT NO. : 5,571,138
DATED : November 5, 1996
INVENTOR(S) : Blomqvist et al.

It is certified that error appears in the above-indentified patent and that said Letters Patent is hereby corrected as shown below:

On the title page, item [73], Assignee: "Stretchex" should read
-- Strechex --

Column 5, line 26, "one way" should read --one-way--.

Column 6, lines 15-16, in claim 4, after "wherein" delete "each first and second end of"

Signed and Sealed this

Fourth Day of February, 1997

Attest:

BRUCE LEHMAN

*Attesting Officer*  *Commissioner of Patents and Trademarks*